United States Patent
Siebenkotten et al.

(10) Patent No.: US 6,521,456 B1
(45) Date of Patent: Feb. 18, 2003

(54) CELLULAR TRANSPORT SYSTEM FOR THE TRANSFER OF A NUCLEIC ACID THROUGH THE NUCLEAR ENVELOPE AND METHODS THEREOF

(76) Inventors: Gregor Siebenkotten, Wilhelm-Waldeyerstrasse 14, Koln, D-50937 (DE); Rainer Christine, Pasteurstrasse 36, Berlin, D-10407 (DE)

( * ) Notice: Subject to any disclaimer, the term of this patent is extended or adjusted under 35 U.S.C. 154(b) by 0 days.

(21) Appl. No.: 09/869,875

(22) PCT Filed: Jan. 3, 2000

(86) PCT No.: PCT/DE00/00061

§ 371 (c)(1), (2), (4) Date: Jul. 6, 2001

(87) PCT Pub. No.: WO00/40742

PCT Pub. Date: Jul. 13, 2000

(30) Foreign Application Priority Data

Jan. 8, 1999 (DE) .......................................... 199 00 513
Jul. 20, 1999 (DE) .......................................... 199 33 939

(51) Int. Cl.[7] ...................... C07K 14/005; G01N 33/92; C12N 15/74

(52) U.S. Cl. ...................... 435/455; 436/71; 435/320.1; 530/350

(58) Field of Search .............................. 435/455, 320.1; 514/44; 436/71; 536/23.1, 23.7, 24.1, 24.2; 530/350

(56) References Cited

U.S. PATENT DOCUMENTS

| | | | |
|---|---|---|---|
| 5,539,082 A | | 7/1996 | Nielsen et al. |
| 5,631,237 A | | 5/1997 | Dzau et al. |
| 5,670,347 A | * | 9/1997 | Gopal ...................... 435/172.1 |
| 5,736,392 A | | 4/1998 | Hawley-Nelson et al. |
| 6,312,956 B1 | * | 11/2001 | Lanc ........................... 435/455 |

FOREIGN PATENT DOCUMENTS

| | | |
|---|---|---|
| DE | 195 41 679 | 5/1997 |
| WO | WO93/19768 | 10/1993 |
| WO | WO94/13325 | 6/1994 |
| WO | WO96/40961 | 12/1996 |

OTHER PUBLICATIONS

Kolkhof; Specificities of three tight–binding Lac repressors, 1992, Nucleic Acids Research, vol. 20, No. 19: 5035–5039.*
Verma et.al.; Gene therapy– promises, problems and prospects, 1997, Nature, vol. 389: 239–242.*
Marshall; Gene Therapy's Growing Pains, 1995, Science, vol. 269: 1050–1055.*
Orkin et.al.; Report and Recommendations of the Panel to Assess the NIH Investment in Research on Gene Therapy, 1995.*

Aldrian–Herrada et al., "A peptide nucleic acid (PNA) is more rapidly internalized in cultured neurons when coupled to a retro–inverso delivery peptide. The antisense activity depresses the target mRNA and protein in magnocellular oxytocin neurons," *Nucleic Acid Research*, 26:4910–16, 1998 (Exhibit 9).

Batterson, W. et al., "Molecular genetics of herpes simplex virus. VIII. further characterization of a temperature–sensitive mutant defective in release of viral DNA and in other stages of the viral reproductive cycle," *J Virol*, 45:397–407 (Abstract only), 1983 (Exhibit 10).

Boulikas, Teni, "Nuclear Localization Signals (NLS)," *Critical Reviews in Eukaryotic Gene Expression*, 3:193–227, 1993 (Exhibit 11).

Boulikas, Teni, "Nuclear Import of Protein Kinases and Cyclins," *Journal of Cellular Biochemistry*, 60:61–82, 1996 (Exhibit 12).

Boulikas, Teni, "Nuclear Import of DNA Repair Proteins," *Anticancer Research*, 17:843–63, 1997 (Exhibit 13).

Branden, L. J. et al., "A peptide nucleic acid–nuclear localization signal fusion that mediates nuclear transport of DNA," *Nat Biotechnol*, 17:784–7 (Abstract only), 1999 (Exhibit 14).

Chang, Deching et al., "Identification of a Nuclear Localization Sequence in the Polyomavirus Capsid Protein VP2," *Virology*, 191:978–83, 1992 (Exhibit 15).

Chen, Yuh–Ru et al., "The Human DNA–Activated Protein Kinase Phosphorylates Simian Virus 40 T Antigen at Amino– and Carboxy– Terminal Sites," *Journal of Virology*, 65:5131–40, 1991 (Exhibit 16).

Citovsky, Vitaly et al., "Nuclear import of Agrobacterium VirD2 and VirE2 proteins in maize and tobacco," *Proc Natl Acad Sci USA*, 91:3210–4, 1994 (Exhibit 17).

Collas, Philippe et al. "The nuclear localization sequence of the SV40 T antigen promotes transgene uptake and expression in zebrafish embryo nuclei," *Transgenic Research*, 5:451–8, 1996 (Exhibit 18).

Collas, Philippe and Peter Aleström, "Nuclear Localization Signal of SV40 T Antigen Directs Import of Plasmid DNA into Sea Urchin Male Pronuclei In Vitro," *Molecular Reproduction and Development*, 45:431–8, 1996 (Exhibit 19).

(List continued on next page.)

*Primary Examiner*—Remy Yucel
*Assistant Examiner*—Sita Pappu
(74) *Attorney, Agent, or Firm*—Mandel & Adriano

(57) ABSTRACT

The present invention relates to a nuclear transport agent, to a gene transfer system comprising said nuclear transport agent, to a method for transporting DNA into the nucleus of eukaryotic cells using said nuclear transport agent and to the use of said nuclear transport agent in gene therapy for treating cancer, viral infections, diseases of the nervous system, graft rejection and monogenic or polygenic hereditary diseases.

16 Claims, 4 Drawing Sheets

Collas, P and P Aleström, "Rapid targeting of plasmid DNA to zebrafish embryo nuclei by the nuclear localization signal of SV40 T antigen," *Mol Mar Biol Biotechnol*, 6:48–58 (Abstract only), 1997 (Exhibit 20).

Collas, P and P Aleström, "Nuclear localization signals: a driving force for nuclear transport of plasmid DNA in zebrafish," *Biochem Cell Biol*, 75:633–40 (Abstract only), 1997 (Exhibit 21).

Dowty, Martin E. et al., "Plasmid DNA entry into postmitotic nuclei of primary rat myotubes," *Proc Natl Acad Sci USA*, 92:4572–6, 1995 (Exhibit 22).

Ellison, Viola and Patrick O. Brown, "A stable complex between integrase and viral DNA ends mediates human immunodeficiency virus integration in vitro," *Proc Natl Acad Sci USA*, 91:7316–20, 1994 (Exhibit 23).

Emi, Nobuhiko et al., "Gene Transfer Mediated by Polyarginine Requires a Formation of Big Carrier–Complex of DNA Aggregate," *Biochemical and Biophysical Research Communications*, 231:421–4, 1997 (Exhibit 24).

Fieck, Annabeth et al., "Modifications of the *E. coli* Lac repressor for expression in eukaryotic cells: effects of nuclear signal sequences on protein activity and nuclear accumulation," *Nucleic Acids Research*, 20:1785–91, 1992 (Exhibit 25).

Friedmann, T., "Gene therapy for neurological disorders," *Trends Genet*, 10:210–4 (Abstract only), 1994 (Exhibit 26).

Friedmann, Theodore, "Human gene therapy—an immature genie, but certainly out of the bottle," *Nature Medicine*, 2:144–7, 1996 (Exhibit 27).

Fritz, Jeffery et al., "Gene Transfer into Mammalian Cells Using Histone–Condensed Plasmid DNA," *Human Gene Therapy*, 7:1395–1404, 1996 (Exhibit 28).

Gallay, Philippe et al., "Role of the Karyopherin Pathway in Human Immunodeficiency Virus Type 1 Nuclear Import," *Journal of Virology*, 70:1027–32, 1996 (Exhibit 29).

Greber U. F. et al., "Stepwise dismantling of adenovirus 2 during entry into cells," *Cell*, 75:477–86 (Abstract only), 1993 (Exhibit 30).

Görlich, Dirk et al., "A 41 amino acid motif in importin-α confers binding to improtin-β and hence transit into the nucleus," *The EMBO Journal*, 15:1810–7, 1996 (Exhibit 31).

Görlich, Dirk, "Transport into and out of the cell nucleus," *The EMBO Journal*, 17:2721–7, 1998 (Exhibit 32).

Jans, David A. et al., "p34$^{cdc2}$–mediated Phosphorylation at T$^{124}$ Inhibits Nuclear Import of SV–40 T Antigen Proteins," *The Journal of Cell Biology*, 115:1203–11, 1991 (Exhibit 33).

Kaneda, Yasufumi et al., "Increased Expression of DNA Conintroduced with Nuclear Protein in Adult Rat Liver," *Science*, 243:375–8, 1989 (Exhibit 34).

Kolkhof, Peter, "Specificities of three tight–binding Lac repressors," *Nucleic Acid Research*, 20:5035–9, 1992 (Exhibit 35).

Lanford, Robert E. et al., "Induction of Nuclear Transport with a Synthetic Peptide Homologous to the SV40 T Antigen Transport Signal", *Cell*, 15:575–82, 1986 (Exhibit 36).

Lartey, R. and V. Citovsky, "Nucleic acid transport in plant–pathogen interactions," *Genet Eng (NY)*, 19:201–14 (Abstract only), 1997 (Exhibit 37).

Mistry, A. R. et al., "Recombinant HMG1 Protein Produced in *Pichia pastoris*: A Nonviral Gene Delivery Agent," *BioTechniques*, 22:718–29, 1997 (Exhibit 38).

Morris, M. C. et al., "A new peptide vector for efficient delivery of oligonucleotides into mammalian cells," *Nucleic Acid Research*, 25:2730–6, 1997 (Exhibit 39).

Nakanishi, Akira et al., "Association with capsid proteins promotes nuclear targeting of simian virus 40 DNA," *Proc Natl Acad Sci USA*, 93:96–100, 1996 (Exhibit 40).

Naldini, L. et al., "In vivo gene delivery and stable transduction of nondividing cells by a lentiviral vector," *Science*, 272:263–7 (Abstract only), 1996 (Exhibit 41).

Neumann, Gabrielle et al., "Nuclear Import and Export of Influenza Virus Nucleoprotein," *Journal of Virology*, 71:9690–700, 1997 (Exhibit 42).

Nielsen, P. E. et al., "Sequence–selective recognition of DNA by strand displacement with a thymine–substituted polyamide," *Science*, 254:1497–500 (Abstract only), 1991 (Exhibit 43).

Niidome, Takuro et al., "Binding of Cationic α–Helical Peptides to Plasmid DNA and Their Gene Transfer Abilities into Cells," *The Journal of Biological Chemistry*, 272:15307–12, 1997 (Exhibit 44).

Reiss, B. et al., "Targeting of a functional *Escherichia coli* RecA protein to the nucleus of plant cells," *Mol Gen Genet*, 253:695–702, 1997 (Exhibit 45).

Rihs, Hans–Peter and Reiner Peters, "Nuclear transport kinetics depend on phosphorylation–site–containing sequences flanking the karyophilic signal of the Simian virus 40 T–antigen," *The EMBO Journal*, 8:1479–84, 1989 (Exhibit 46).

Rihs, Hans–Peter et al., "The rate of nuclear cytoplasmic protein transport is determined by the casein kinase II site flanking and nuclear localization sequence of the SV40 T–antigen," *The EMBO Journal*, 10:633–9, 1991 (Exhibit 47).

Sebestyén, Magdolna G. et al., "DNA vector chemistry: The covalent attachment of signal peptides to plasmid DNA," *Nature Biotechnology*, 16:80–5, 1998 (Exhibit 48).

Shuman, Stewart, "Novel Approach to Molecular Cloning and Polynucleotide Synthesis Using Vaccinia DNA Topoisomerase," *The Journal of Biological Chemistry*, 269:32678–84, 1994 (Exhibit 49).

Sorgi, F. L. et al., "Protamine sulfate enhances lipid–mediated gene transfer," *Gene Therapy*, 4:961–8, 1997 (Exhibit 50).

Trubetskoy, Vladimir S. et al., "Self–assembly of DNA–polymer complexes using template polymerization," *Nucleic Acid Research*, 26:4178–85, 1998 (Exhibit 51).

Wadhwa, Manpreet S. et al., "Peptide–Mediated Gene Delivery: Influence of Peptide Structure on Gene Expression," *Bioconjugate Chem*, 8:81–8, 1997 (Exhibit 52).

Wang, Ping et al., "The NPI–1/NPI–3 (Karyopherin α) Binding Site on the Influenza A Virus Nucleoprotein NP Is a Nonconventional Nuclear Localization Signal," *Journal of Virology*, 71:1850–6, 1997 (Exhibit 53).

Weis, Karsten et al., "The conserved amino–terminal domain of hSRP1α is essential for nuclear protein import," *The EMBO Journal*, 15:1818–25, 1996 (Exhibit 54).

Wilke, M. et al., "Efficacy of a peptide–based gene delivery system depends on mitotic activity," *Gene Ther*, 3:1133–42 (Abstract only), 1996 (Exhibit 55).

Xiao, Chong–Yun et al., "SV40 Large Tumor Antigen Nuclear Import Is Regulated by the Double–stranded DNA–dependent Protein Kinase Site (Serine 120) Flanking the Nuclear Localization Sequence," *The Journal of Biological Chemistry*, 272:22191–8, 1997 (Exhibit 56).

Yoneda, Y. et al., "Synthetic peptides containing a region of SV 40 large T–antigen involved in nuclear localization direct the transport of proteins into the nucleus," *Exp Cell Res*, 170:439–52 (Abstract only), 1987 (Exhibit 57).

Yoneda, Yoshihiro et al., "A Long Synthetic Peptide Containing a Nuclear Localization Signal and Its Flanking Sequences of SV40 T–Antigen Directs the Transport of IgM into the Nucleus Efficiently," *Experimental Cell Research*, 201:313–20, 1992 (Exhibit 58).

* cited by examiner

CELLULAR TRANSPORT SYSTEM FOR THE TRANSFER OF A NUCLEIC ACID THROUGH THE NUCLEAR ENVELOPE AND METHODS THEREOF

This application claims benefit of International Application No. PCT/DE00/00061, filed Jan. 3, 2000; which claims priority of German Applications No. 199 33 939.2, filed on Jul. 20, 1999 and 199 00 513.3 filed on Jan. 8, 1999. The contents of all of the foregoing applications in their entireties are incorporated by reference into the present application.

The present invention relates to a nuclear transport agent, to a gene transfer system comprising said nuclear transport agent, to a method for transporting DNA into the nucleus of eukaryotic cells using said nuclear transport agent and to the use of said nuclear transport agent in gene therapy for treating cancer, viral infections, diseases of the nervous system, graft rejection and monogenic or polygenic hereditary diseases.

The active transport into the nucleus is necessary for the transfer of genetic material into all cells that do not divide in the period before the intended expression of the genetic material. A nuclear transport system for nucleic acids is very important because it facilitates the efficient transfer of DNA into those cells that divide rarely or not at all (Dowty et al., 1995, Wilke et al., 1996). Most primary cells belong to this group. Primary cells are of highest scientific interest for two reasons. Firstly, said cells that have freshly been isolated from an organism reflect the functional state of the cell type much better than cell lines derived therefrom. Secondly, they are the target cells for gene therapy. In addition, a nuclear transport system increases the efficiency of DNA transfer into established cell lines by enabling also those cells to express transferred genetic material, which have not divided in the period of time between start of transfer and analysis.

Genetic material is active in the nucleus. The transport therein can either occur coincidentally during cell division when the nuclear envelope temporarily disintegrates in the course of mitosis or it has to take place actively.

1) Nuclear Proteins are Transported into the Nucleus by Means of Nuclear Localization Signals The double membrane that envelops the nucleus has pores. Little molecules can pass through these pores by diffusion. In order to be able to enter the nucleus, proteins larger than about 50 kDa need a nuclear localization signal (NLS) that has to be recognized by the transport machinery. Typically, a sufficient signal consists of four to eight amino acids, is rich in the positive amino acids arginine and lysine and contains prolines. It is strongly conserved in evolution so that mammalian NLS are also functional in yeast. Heterologous NLS can also be used as a tool to transport target molecules into the nucleus. For this purpose, NLS can be incorporated into the sequences of cytoplasmic proteins at relatively random positions or can be coupled chemically to proteins or even gold particles (reviewed in Görlich, 1998).

2) Many Viruses Use Nuclear Protein Transport Machinery of the Cell for the Transport of Their DNA into the Nucleus HIV and other lentiviruses that are able to infect resting cells use viral proteins and the cellular transport machinery to transfer their DNA into the nucleus. The NLS in Vpr and matrix protein of the HIV pre-integration complex (Gallay et al., 1996) are essential for the infection of cells that do not divide (Naldini et al., 1996). Although little is known about how viruses transfer their genomes into the nucleus, the help of viral structural proteins containing NLS might even be a general principle. This is also suggested by the following observations: A specific mutation in the HSV capsid protein prevents the transport of viral DNA into the nucleus (Batterson et al., 1983). Adenovirus DNA is transported into the nucleus together with the hexon protein of the disintegrated capsid (Greber et al., 1993). The transport of SV40 DNA into the nucleus is mediated by a viral protein (probably Vp3) that remains associated with DNA (Nakanishi et al., 1996). Two bacterial proteins containing NLS are responsible for the import of *Agrobacterium tumefaciens* T-DNA into plant nuclei (Citovsky et al., 1994).

Due to the ability of some viruses to infect resting cells, mutant variants of, for example, HIV, adenovirus and herpes virus are used as DNA transfer vehicles for the development of gene therapy approaches. Firstly, this involves the risk of immunological reactions to virus components (Friedmann, 1994, 1996) and, secondly, helper cell lines are used in such systems for which the release of less mutated virus genomes cannot be excluded. Moreover, the handling of these systems is difficult.

Several artificial systems have been described that are supposed to increase transfection efficiency by means of peptides or proteins containing nuclear localization signals.

A) Proteins

Kaneda et al. (1989) and Dzau and Kaneda (1997, U.S. Pat. No. 5,631,237) describe a gene transfer system that is based on the use of Sendai virus, liposomes and added proteins that are meant to support nuclear transport of DNA. For this purpose, the group used HMG-1 (high mobility group 1 protein), a basic non histone protein of chromatin which binds to DNA. HMG-1 binds to DNA through a long basic region. It is localized in the nucleus, but does not have a known NLS. In vitro, HMG-1 protein forms complexes with vector DNA. The production of purified HMG-1 is costly and labor-intensive.

Mistry et al. (1997) describe experiments concerning HMG-1-mediated nuclear transport. Due to its positive charge HMG-1, as a transfection reagent that complexes DNA, is used here for the passage of DNA through the cell membrane. The efficiency is low. The company Wako Bio-Products (Richmond, Va., U.S.A.) sold (1997) the proteins HMG-1 and -2 as additives for lipofection reagents to mediate nuclear transport.

Fritz et al. (1996) followed a similar approach with calf thymus histones or a recombinant protein consisting of SV40 NLS and human histone H1. Both of these proteins evidently form large complexes with DNA, as was shown in the publication, and are suitable for the passage of the cellular membrane but not for nuclear transport.

B) Due to Their Simpler and Less Expensive Production, Synthetic Peptides Containing NLS Sequences Were Used as Well The group of P. Aleström (Collas et al., 1996, Collas and Alestrom, 1996, 1997a, b) uses the NLS peptide from SV40 to complex DNA and have it transported into the nucleus by the cell. This DNA binding occurs solely through the positively charged amino acids of the NLS that are essential for its function. This results in masking the actual signal for the nuclear transport proteins as long as the DNA is complexed with the peptide. An NLS-dependent transport of fluorescently labeled DNA could be observed in isolated male pronuclei formed in vitro from sea urchin sperms, when they have been incubated in the lysate of fertilized zebra fish eggs. At a molecular ratio of $\geq 100:1$ (NLS peptide:vector) and $\geq 1,000$ vector copies per cell, an increase in luciferase expression could be observed in zebra fish embryos, when vector DNA was micro-injected. into the cytoplasm of the cells. (At 100 peptides/vector and 1,000 injected vectors a sixfold increase was obtained as compared to 0 peptide.) Due to the high density, possibly not all NLS bind completely to the DNA and thus parts remain accessible for the transport machinery; this might be the cause why an effect can be perceived at all (cf. Sebastyén et al., 1998). The transport machinery is probably able to recognize signals composed of two peptide sequences (Boulikas, 1993).

Sebastyén et al. (1998) covalently coupled many hundreds of SV40 NLS peptides to DNA molecules, with the NLS being scattered over the entire length of the DNA strand. Due to its massive modification, the DNA can no longer be transcribed. As is discussed in the article, the DNA is evidently only transported into the nucleus when so many NLS peptides are bound that, for steric reasons, not all of them are masked by the interaction with the negative charges of the DNA.

Gopal (U.S. Pat. No. 5,670,347) describes a peptide that consists of a DNA-binding basic region, a flexible hinge region and an NLS. As DNA binding is also in this case achieved by the amino acids' positive charges, the reagent forms complexes with the DNA that are meant to serve at the same time for the transport across the cellular membrane. It is not evident why the NLS sequence should not participate in the binding of DNA so that the actual signal for the nuclear transport proteins is again likely masked by the DNA as long as the peptide is coupled thereto. Moreover, the complexes generated may become very large (Emi et al., 1997, Niidome et al., 1997, Wadhwa et al., 1997, Trubetskoy et al., 1998), which would impair transport through the nuclear pores (Lanford et al., 1986, Yoneda et al., 1987, 1992). An effect beyond the known function of polycationic peptides as a transfection reagent, which supports the passage of DNA through the cellular membrane (Sorgi et al., 1997, cf. Hawley-Nelson et al., 1997) has not been shown.

Gerhard et al. (DE-OS 195 41 679) suggest NLS polylysine conjugates for gene transfer. It is also true in this case, that the emerging complexes consisting of cationic polylysine, cationic NLS and DNA mask the nuclear transport signal as long as it is coupled to the DNA.

Szoka (PCT 1993, claims 23–27) couples NLS peptides to DNA via an intercalating agent. After pre-incubating vector and peptide (ratio of 1:300), the efficiency of lipofection increases four- to fivefold. Due to its highly positive charge, the SV40 peptide used is able to complex DNA. Complexing of DNA with cationic peptides leads to an increased lipofection efficiency by improving the efficiency of passage across the cellular. membrane (Sorgi et al., 1997, cf. Hawley-Nelson et al., 1997). Nuclear transport is rather impaired thereby, at least when large complexes are generated (see above). As the NLS peptides used bind to DNA due to their charge, the recognition of the transport signal by the nuclear transport machinery is impaired (see above). The use of mutagenetic intercalators described in the example restricts the applicability. Szoka suggests additional molecules for transfection that also bind to DNA non-covalently and unspecifically but, as before, cannot prevent the NLS peptide itself from binding to and complexing the DNA. The problem of a direct association of the NLS peptide with the DNA is not discussed.

Hawley-Nelson et al. (U.S. Pat. No. 5,736,392) describe a similar system. An NLS peptide is mixed with vector DNA either directly or after covalent coupling to a DNA-binding molecule. The complexes generated are then used for lipofection (or other transfections). In this system the addition of a polycationic peptide without NLS increases the transfection efficiency even more than the addition of a cationic NLS. The coupling of spermidine to the NLS peptide does result in a further increase in transfection efficiency. Thus, also in this case, the amplification effect is solely explained by the complexing of DNA via cationic peptides. As the presence of NLS does not increase the transfection efficiency any further, it is to be assumed that the recognition sequence for the nuclear transport machinery is masked in this case, as well.

The company TIB Molbiol (leaflet 1998) describes the transport of PNA oligonucleotides with a C-terminal NLS peptide to specifically suppress the expression of selected genes. The NLS serves for the transport of the PNA oligonucleotides into the nucleus so that they can then hybridize with their target sequence.

So far, the known agents for the transport of DNA into the nucleus have the disadvantage that the efficiency is very low. This low efficiency is insufficient to render resting cells transfectable.

DESCRIPTION OF THE INVENTION

Figure 1:
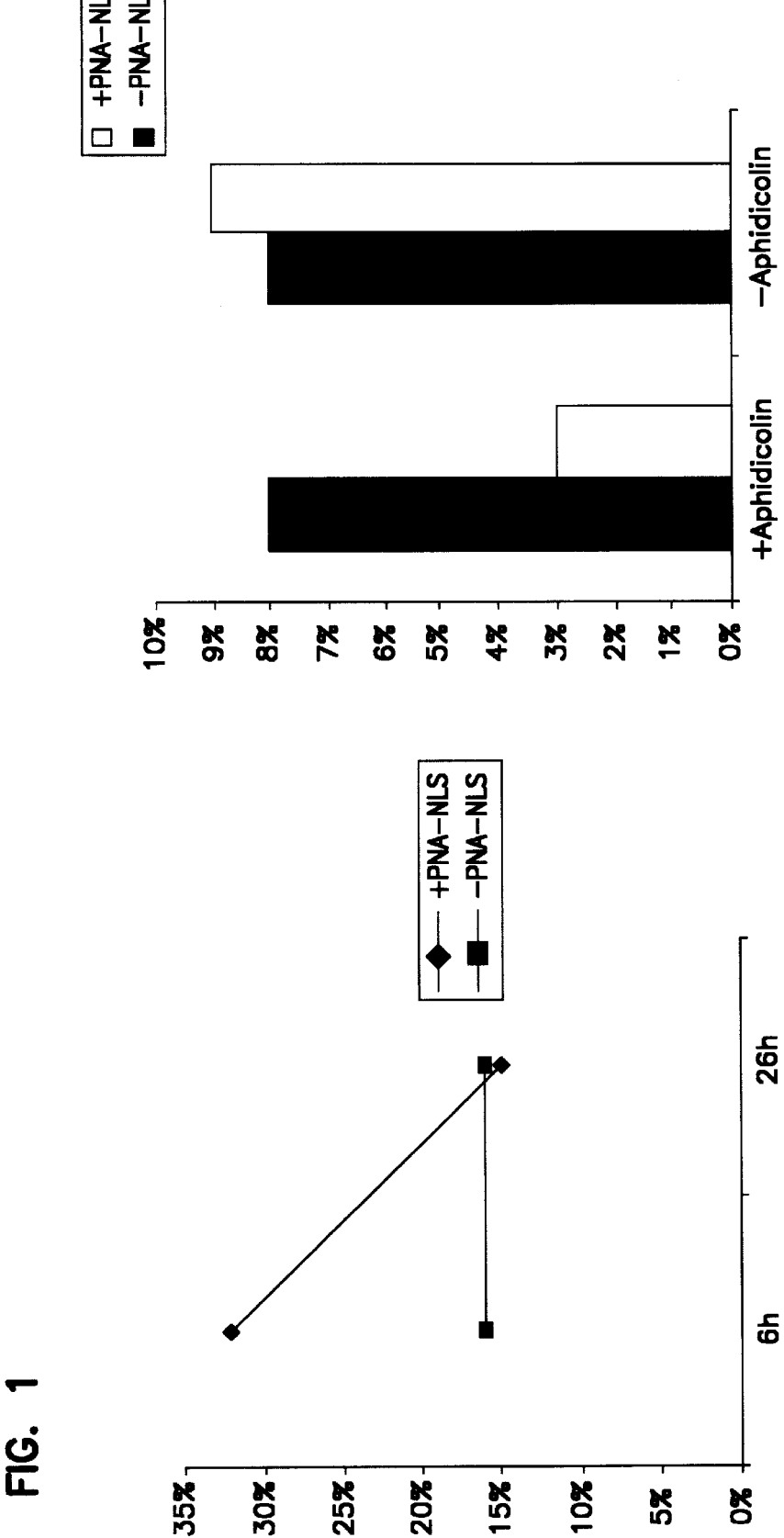
FIG. 1 shows the effect of PNA-NLS on the transfection efficiencies as percent of transfected cells. Transfection of CHO cells with or without PNA-NLS and in the presence or absence of Aphidicholin, as described in Example 3, is shown.

Thus, the problem underlying the present invention is to provide a nuclear transport agent that facilitates the efficient transport of DNA into the nucleus so that also resting or only very slowly dividing cells become transfectable to a useful degree.

This problem is solved by a nuclear transport agent consisting of two modules A and B, where module A binds specifically to DNA and does not lead to the formation of complexes containing more than one DNA molecule by unspecific binding, and where module B contains a nuclear localization signal or a non NLS signal that does not bind to DNA unspecifically. A preferred nuclear transport agent according to the present invention comprises a module A that binds sequence specifically to DNA and/or binds specifically to DNA ends. Particularly preferred is a nuclear transport agent where module A is a synthetic peptide, a protein or a peptide nucleic acid (PNA).

In a further embodiment of the nuclear transport agent according to the present invention, module B contains an extended nuclear localization signal that does not form complexes with DNA due to its charges. A nuclear transport agent is preferred in which module B contains an extended nuclear localization signal that possesses an approximately neutral net charge. A nuclear transport agent is particularly preferred in which module B contains an extended nuclear localization signal that comprises a nuclear localization signal and flanking negatively charged amino acids. A NLS sequence does not have to be identical to a naturally occurring NLS sequence but can also be an amino acid sequence based on theoretical consideration as long as it is functional as NLS. Moreover, module B can contain peptide sequences or non-peptide components that do not directly belong to the nuclear localization signal or extended nuclear localization signal. Preferred is a component that increases the distance between the nuclear localization signal and module A.

Moreover, the invention concerns a gene transfer system comprising a nuclear transport agent according to the present invention and a cationic lipid, peptide, polyamine or cationic polymer.

Moreover, the invention concerns a method for the transport of DNA into the nucleus of eukaryotic cells, preferably primary cells, wherein the cells are transfected with the DNA to be transported and the nuclear transport agent according to the present invention by methods known in the art.

A further embodiment concerns the use of the nuclear localization agent according to the present invention in gene therapy, in particular for the treatment of cancer, viral infections, diseases of the nervous system, graft rejection as well as monogenic or polygenic hereditary diseases.

The expression "unspecific binding of the nuclear localization signal to DNA", as used in the present invention, denotes an association that prevents the nuclear localization signal from being completely recognizable to the nuclear transport machinery.

The expression "specific binding of module A to DNA", as is used in the present invention, denotes, firstly, sequence-specific binding, in which the sequence of DNA nucleotides is crucial for the interaction and, secondly, a covalent binding with DNA that is mediated by DNA single or double strand ends.

The expression "extended nuclear localization signal", as is used in the present invention, denotes that a nuclear localization signal possesses additional flanking amino acids. Preferred is an extended nuclear localization signal that possesses 2 to 40, preferably 4 to 20, additional flanking amino acids.

The expression "extended nuclear localization signal that does not form complexes with DNA due to its charge", as is used in the present invention, denotes that module B contains a nuclear localization signal whose charges are distributed in such a way that it does not interact with DNA unspecifically and thus remains completely accessible for the nuclear transport machinery.

The expression "approximately neutral net charge", as is used in the present invention, denotes that the extended part of the nuclear localization signal possesses negatively charged amino acids to balance the positive charge of the actual nuclear localization signal so that no more than three positive surplus charges occur in the entire region of the extended nuclear localization signal.

The nuclear transport agent according to the present invention has the advantage that it does not lead to complexing of DNA. It is a further advantage that the nuclear localization signal remains freely accessible to the nuclear transport machinery. Avoiding large DNA complexes that impair nuclear transport and the accessibility of the nuclear localization signals to the nuclear transport machinery when using the nuclear transport agents according to the present invention, leads to a clearly more efficient transport of DNA into the nucleus.

According to the present invention neither the DNA-binding part (module A) nor the nuclear localization signal (module B) leads to the formation of large DNA complexes.

Module A

Module A binds specifically to DNA and does not lead to the formation of complexes with more than one DNA molecule. Module A binds either sequence specifically (i.e. not unspecifically only due to positive charges) or covalently to DNA ends.

Module A can be a peptide of varying lengths or a protein or a PNA sequence (Nielson et al., 1991) or another substance that binds to nucleic acids in a sequence-specific manner. Moreover, module A can be a recombinant protein that binds to DNA specifically, as for example lac repressor or a high-affinity mutant thereof (Kolkhof, 1992, Fieck et al., 1992), or a retroviral integrase that binds sequence specifically to DNA ends (with an LTR core sequence) (Ellison and Brown, 1994).

Covalent binding to the end of a DNA strand can be mediated biologically, for example by topoisomerase I of the poxvirus, if the end of a linear DNA strand has a sequence that is a "suicide substrate" and permits cleavage by topoisomerase but no relegation (Shuman, 1994).

Module B

Module B is a nuclear localization signal or a non NLS signal that does not bind unspecifically to DNA.

The term non NLS signals according to the present invention denotes signals which are not nuclear localization signals but with regard to transfection, gene therapy or DNA vaccination serve to transport the DNA into the cell or to transport DNA within the cell.

The following belongs to non NLS signal: ligands for cellular surface structures, which are able to mediate DNA uptake, e.g. receptor mediated DNA uptake; peptides which destabilize membranes, e.g. to promote premature exit of DNA from endosomes; signals mediating in the cell binding to transport structures to favor intracellular transport to the nucleus.

The nuclear localization signal is preferably an extended nuclear localization signal (as defined above) that does not form complexes with DNA due to its charge or spatial orientation to DNA binding module A. The nuclear localization signal can be generated synthetically or can be part of a protein.

In a nuclear localization signal as is used in the nuclear transport agent according to the present invention, signal sequences—with and without flanking regions—are used that do not bind to DNA via their positive charges in such a way that these charges which are an essential part of most nuclear localization signals, are masked as signals for the nuclear transport machinery.

Apart from the nuclear localization signal or non NLS signal, module B may contain peptide sequences and non-peptide components that are not part of the nuclear localization signal or the extended nuclear localization signal. Preferably, they permit a better steric positioning of the nuclear localization signal, especially an increased distance to the DNA molecule.

Extended sequences of classic NLS are well suited provided that the peptide's net charge can almost be balanced by flanking negatively charged amino acids. These amino acids can occur naturally at these positions in the protein or may have been introduced on the basis of structural considerations. In the original context, negative amino acids are located adjacent to many NLS core sequences (Xiao et al., 1997). It could be shown for an NLS from SV40 which is the most thoroughly investigated NLS, that these flanking sequences clearly increase the efficiency of nuclear transport (Rihs and Peters, 1989, Rihs et al., 1991, Chen et al., 1991, Jans et al., 1991, Xiao et al., 1997). A large protein (IgM)

was transported into the nucleus only after coupling it chemically to the SV40 NLS that had been extended by adjacent sequences, but not after coupling it to the SV40 core NLS peptide (Yoneda et al., 1992).

If the NLS is part of a protein that binds sequence specifically to DNA, the risk with these sequence(s) of being masked by DNA is relatively low. But due to the higher efficiency, extended NLS sequences can also be used in this case.

Non-classic NLS, as for example the NLS from the influenza virus nucleoprotein (Wang et al., 1997, Neumann et al., 1997) which do not have a large excess of positive charges or do not reach the nucleus via the conventional route of transport can also be used.

An (incomplete) overview of NLS as they are intended here is given by T. Boulikas (1993, 1996, 1997).

Finally, nuclear transport signals can be used that are taken from components of the nuclear transport machinery itself, as for example the importin β binding domain (IBB) of importin α. Via this domain, the NLS binding protein importin α is linked to the rest of the nuclear transport machinery (Görlich et al., 1996, Weiss et al., 1996).

In a further preferred embodiment a non NLS signal via PNA (as module A) is bound to existing vector sequences. The binding between PNA and vector is sequence specific. This allows coupling of such non NLS signals to almost all conventional expression vectors without the need to modify them.

For sequence specific binding of PNA to the DNA only those DNA sequences of the vector are used, the masking of which by PNA does not substantially impair the intended purpose of the DNA.

In the case of expression vectors, in particular sequences in the plasmid backbone are used especially those which are present in most conventional expression vectors (e.g. promoter of ampicillin resistance gene). However, also binding in the non coding strand of the expression region is possible. An advantage of the sequence specific binding is a simple and rapid binding of the PNA-peptide-hybrid to the DNA. Example 2 demonstrates for example a simple and rapid binding reaction (5 min, 65° C.) of PNA-peptide-hybrids to double stranded DNA. There may be a spacer between the PNA portion and the actual signal. The spacer may serve to increase the distance of signal to DNA, e.g. to reduce steric hindrance. The spacer may also serve to introduce a predetermined breaking point, e.g. to allow the separation of a ligand in the endosomal milieu, via which the DNA is bound to an endocytosed cell surface receptor.

For the first time, the present invention renders resting or slowly dividing cells transfectably to a percentage that allows subsequent analysis. Most cells freshly isolated from the body of an animal or human (primary cells) do not divide at all or so rarely that DNA, after it has been transported across the cellular membrane successfully, is inactivated before it reaches the nucleus and can be expressed. So far this has led to primary cells being untransfectable unless they were artificially stimulated to proliferate in culture. The unavoidable consequence of this is that these cells then deviate from their original state. A method for the transfection of primary cells permits the analysis of genetic material under the original conditions of a body cell. This is of paramount importance for the investigation of genetic mechanisms and the study of processes inside a body cell.

The teaching according to the present invention that renders primary cells transfectable is also an essential step toward a completely artificial gene transfer system for gene therapy. Such a gene transfer system must have three functional components: one component for the passage of DNA through the cellular membrane, for which cationic lipids and other cationic polymers have proved to be relatively suitable. It has to contain a further component for the transfer of the DNA into the nucleus of the (usually non-dividing) target cells and a third component that mediates the integration of the DNA into the genome. In the present invention for the first time an efficient agent is described that can serve as the second component. A completely artificial gene transfer vehicle that can be employed in gene therapy is expected to be produced easier and less expensive and handled easier than the viral systems currently used, and it is not subject to the immanent risks of these systems. Gene therapeutic approaches have been suggested, for example, for the treatment of cancer, AIDS and various hereditary diseases and will play a significant role in medicine.

The nuclear transport agents described according to the present invention also increase the transfection efficiency in such cultured cells that up to now have already been transfectable by making those cells accessible to the uptake of DNA that do not divide in the period between the passage of the DNA through the cellular membrane and analysis. This is important because even for many established cell lines an increase in transfection efficiency would facilitate the analysis and help lower costs due to the reduced amount of cell material required. Of course, this is also true for all stages in between primary cells and established cell lines.

The following examples illustrate the invention and are not intended to limit the scope thereof.

EXAMPLE 1

PNA-peptide-hybrids

NLS PNA nuclear transport agents were used. PNA sequences were used that are capable of invading DNA double strands (Nielson et al., 1991, Nielson, U.S. Pat. No. 5,539,082).

In the plasmid backbone of almost all expression vectors, two sequences that are well suited for a high-affinity association with PNA are located in the ampicillin resistance gene and the origin of replication.

As peptide components the peptides employed contain: either

1) "SV21" $NH_2$-GKPTADDQHSTPPKKKRKVED-COOH (peptide 1, SEQ ID NO:1), or

2) "SV27" $NH_2$-GKPSSDDEATADSQHSTPPKKKRKVED-COOH (peptide 2; SEQ ID NO:2).

The following PNA sequence is located at the N-terminus of each peptide. Either

A) "ori" $NH_2$-CCTTTCTCCCTTC-peptide (SEQ ID NO:3), or

B) "ssp" $NH_2$-CTCTTCCTTTTTC-peptide (SEQ ID NO:4), or

C) the peptide-PNA hybrid sequence $NH_2$-CCTTT-GGGGGGG-TTTCC-peptide (CCTTT (SEQ ID NO:5); GGGGGGG (SEQ ID NO:10); TTTCC (SEQ ID NO:11)) that has about 30 binding sites in an average expression vector (5 kb) (G=the amino acid glycine).

5 μg of vector DNA solubilized in water were incubated in 10 μl 25 μM NLS-PNA for 10 min at 60° C. The reaction mixture was then adjusted to 250 μl with RPMI.

$5 \times 10^6$ Chinese hamster ovary (CHO) cells that were 60 to 80% confluent were detached with 5 mM EDTA, washed in 15 ml PBS (centrifuged at 50×g for 10 min). The pellet was resuspended in 250 μl RPMI and mixed with the pre-incubated DNA, transferred to an electroporation cuvette (gap width of 0.4 cm) and incubated at room temperature for 10 min. After electroporation (210 V, 975 μF, BioRad GenePulser) the cuvette was incubated at 37° C. for another 10 min before the cells were seeded in pre-warmed medium.

In order to show unequivocally that those cells were transfected that had not divided between the start of the experiment and analysis, cells were transfected with pMACS 4.1 (an expression vector for human CD4) according to the method described and cell division was assessed as follows: Before transfection, cells were labeled with green fluorescence by incubation in 1 μM carboxyfluorescein diacetate succinimide ester (CFDA, SE) (Molecular Probes, Eugene, U.S.A.). The brightness of the cells is reduced to 50% by cell division. Using a flow cytometer (FACSCalibur), it was determined on the single-cell level that also cells that had not divided (100% green fluorescence) expressed the transfected gene (dark red fluorescence after staining with anti-CD4 antibody coupled to Cy5).

EXAMPLE 2
Rapid Binding of PNA-NLS to Existing Vector Sequences

PNA-peptide-hybrids were coupled to double stranded DNA.

An existing vector sequences can be labelled via PNA almost quantitatively (>90%) with an NLS-peptide within 5 minutes. To achieve binding of heat labile components via PNA, incubating for one hour at 37° C. is sufficient to label most of the DNA (Table 1).

100 ng expression vector were incubated in TE (pH 7,8) with 25 μM of different PNA-peptide-hybrids at either 65° C. or 37° C. for five minutes to three hours. The PNA-sequence $NH_2$-CTCTTCCTTTTTC-COOH (SEQ ID NO: 6) used here, binds to the promoter of the ampicillin resistance gene.

At the C-terminus either a peptide of 21 amino acids (Peptide 1) or 27 amino acids (Peptide 2) or a spacer of 10 AEEA-units (Fmoc-AEEA-OH Spacer, PerSeptive Biosystems Inc., Framingham, USA) followed by 27 amino acids (Peptide 3) is located. The binding assays were subsequently incubated with restriction endonuclease EarI. Restricted DNA was stained with YOYO (Molecular Probes, Inc., Eugene, Oreg., USA) separated on an agarose gel and quantified with a fluorescence scanner (Image Plate Reader FLA 2000, analysis software L-Process, version 1.6, Fuji Photo Film Co., Ltd., Tokio). Cleavage of DNA by restriction endonuclease EarI is inhibited at the PNA binding site. Additional EarI restriction sites serve as internal control of the reaction.

TABLE 1

| Portion of peptide-labelled DNA shown as percentage of input DNA | | | | |
| --- | --- | --- | --- | --- |
| ° C. | min. | Peptide 1 | Peptide 2 | Peptide 3 |
| 65 | 5 | 94% | 96% | 91% |
|  | 10 | 96% | 97% | 95% |
|  | 15 | 96% | 97% | 95% |
| 37 | 60 | 85% | 90% | 74% |
|  | 120 | 91% | 91% | 76% |
|  | 180 | 94% | 94% | 90% |

The binding reaction of PNA to DNA is simple, robust and rapid. The binding is almost irreversible and therefore suitable for cellular transport processes. Compared to proteins, peptides and PNA can be synthesised less expensively and can be stored easier and for a longer time.

EXAMPLE 3
Transfection Using PNA-NLS

In dividing cell lines active nuclear transport of transfected DNA provokes its sooner expression compared to DNA which is not transported. Provided that the transfected DNA survives in the cytoplasm for a time long enough, the expression rates of transfected DNA in rapidly dividing cells with and without nuclear transport reagent should approximate little by little. The reason for this is the fact that transfected DNA that remains in the cytoplasm can reach the nucleus during cell division. Using aphidicolin the division activity and the transfection ability of cells can be strongly reduced. Active nuclear transport abolishes this effect of reduced transfection efficiency.

For electroporation 5 μg of linearized vector-DNA, dissolved in water, were incubated in a final volume of 10 μl with or without 25 μM PNA-NLS (Peptide 3: $NH_2$-(AEEA)$_{10}$-GKPSSDDEATADSQHSTPPKKKRKVED-COOH; (SEQ ID NO:7)) for 10 min at 65° C. The further procedure was as described in example 1.

For lipofection 3 μg of vector-DNA, dissolved in water, were incubated in a final volume of 10 μl with or without 25 μM PNA-NLS (Peptide 3) for 10 min at 65° C. Transfection with lipofectamine (Life Technologies GmbH, Karlsruhe) was done according to the manufacturer's instructions.

To inhibit division of CHO cells substantially, cells were incubated without serum for 24 hours followed by a 12-hour-incubation with serum and 20 μg/ml aphidicolin (Sigma-Aldrich Chemie GmbH, Deisenhofen). All subsequent steps of lipofection were done in the presence of 20 μg/ml aphidicolin. The results of transfection are shown in FIG. 1.

Two electrically neutral NLS, which are coupled to a sequence present in most of the expression vectors are capable of duplicating the percentage of transfected cells early after transfection although only a few cells have divided. Reduction of transfection efficiency caused by the reduction of cell division rate using aphidicolin can be abolished in this way.

EXAMPLE 4
Sequence-specific-binding NLS-fusionprotein

A high-affinity binding mutant of the *E.coli* lac repressor was used as sequence-specific DNA-binding protein. This mutant has a binding constant of $10^{-15}$ M for the lac operator sequence (Kolkhof, 1992). The high affinity is achieved by an amino acid replacement of serine 61 to leucine.

The nuclear transport proteins used here have a deletion of the last thirty C-terminal amino acids (position 331–360) and a replacement of leucine at position 330 to serine. These mutant proteins form homodimers instead of homotetramers and therefore contain one single DNA-binding site instead of two sites. But also tetramers may be used as nuclear transport agent of the invention.

The dimer-variants each were extended at the N-terminus for one NLS:

"N1D" NLS1: MPKKKRKV-MKPVTLYDVA . . .

"N2D" NLS2: MEEDTPPKKKRKVEDL-KPVTLYDVA . . .

The NLS-sequences are shown in bold and correspond to SEQ ID NO: 8 and SEQ ID NO: 9, respectively. Sequences MKPVTLYDVA (SEQ ID NO:12) . . . and KPVTLYDVA (SEQ ID NO:13) . . . indicate the *E.coli* lac repressor specified above.)

NLS1 corresponds to the NLS of the SV40 virus large T antigen. NLS2 represents a hybrid with neutral net charge consisting of the SV40-NLS and the N-terminal flanking region of the NLS from Polyoma virus VP2-protein.

Lac-operator-sequences can be found in a number of expression vectors and can easily be joined to any sequence as extensions of PCR primers.

EXAMPLE 5
DNA-binding of Lac-repressor Mutants Containing NLS

The following lac-operator-sequences were used for binding assays:

The naturally occurring operator: AATTGTGAGC GGATAACAATT (SEQ ID NO:14) and a perfectly palindromic operator-sequence: AATTGTGAGC GCTCACAATT (SEQ ID NO: 15).

Figure 2:
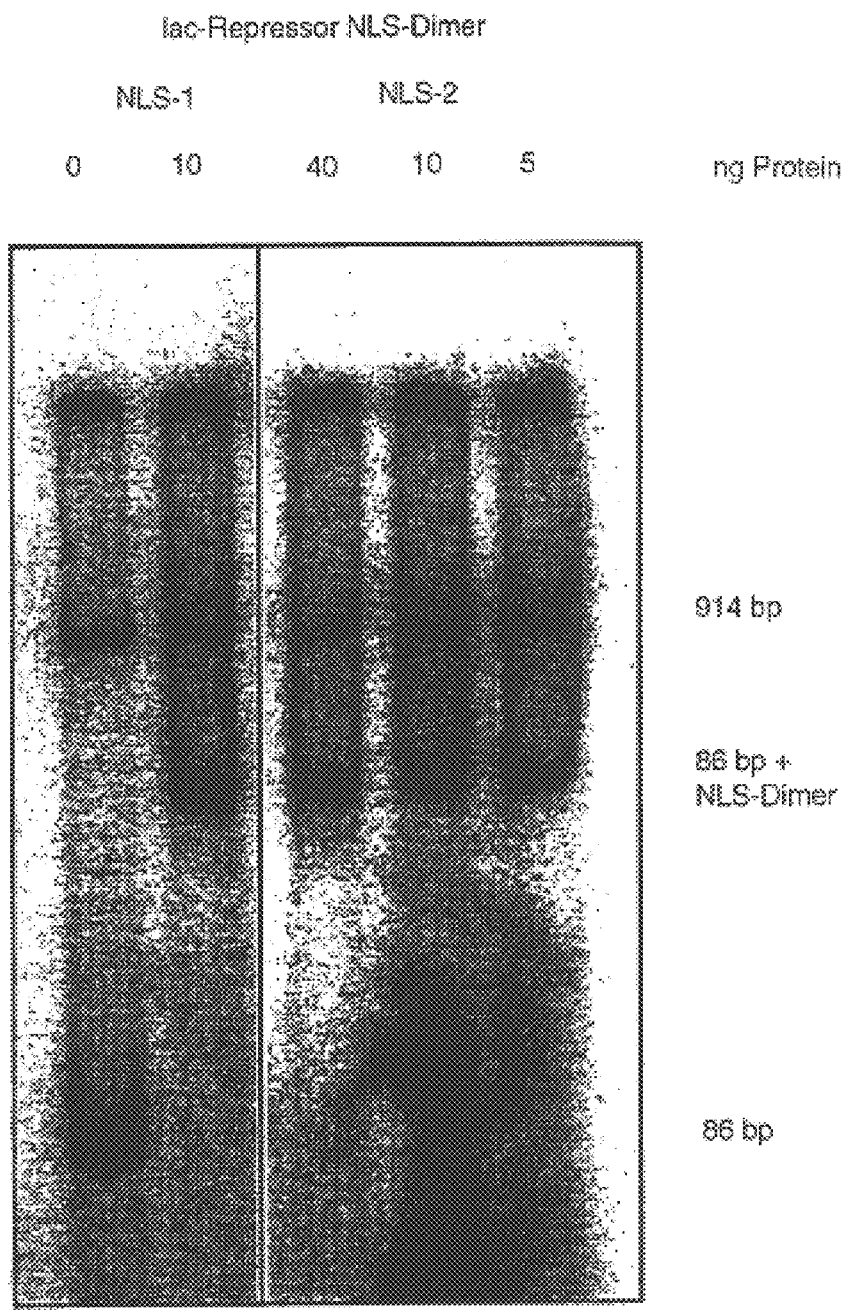
FIG. 2 shows an autoradiograph of a DNA-retardation gel of a DNA-binding assay with mutated lac-repressor protein containing different NLS, as described in Example 5.

0.7 ng of a radioactively labelled DNA-fragment of 1 kb length was cleaved by restriction endonucleolytic digestion into fragments of 914 bp and 86 bp length and then incubated for 30 min at room temperature with lac-repressor NLS-1-dimer or NLS-2-dimer, respectively. The fragments were then separated on a polyacrylamide gel (FIG. 2). The 86 bp-fragment, which contains the lac-operator, is retarded, due to specific binding. Non-specific binding results in retardation of the 914 bp-fragment lacking the lac-operator. In the case of complete specific binding hardly any non-specific binding is observed.

Further experiments demonstrated, that stable binding is achieved using various conditions e.g. in cell culture medium RPMI, 150 mM sodium chloride or a buffer consisting of 10 mM Tris/HCl (pH 7.2), 10 mM potassium chloride and 3 mM magnesium acetate with both tested operator-sequences.

EXAMPLE 6
Nuclear Transport of DNA by Lac-repressor-NLS

Approximately 8 $\mu$g (100 pmol) lac-repressor-NLS-mutants were incubated with 2 $\mu$g (100 pmol) double-stranded DNA of 30 bp length, labeled at both ends with the fluorescent dye Cy5, for 30 min at room temperature in a total volume of 300 $\mu$l 10 mM Tris/HCl (pH 7.2), 10 mM KCl, 3 mM Mg-Acetate and 50 $\mu$g/ml BSA. Unbound DNA was separated by centrifugation through a Microcon-filter (Amicon). The buffer of the sample was then changed to cell injection buffer (76 mM $K_2HPO_4$, 17 mM $KH_2PO_4$, 14 mM $NaH_2PO_4$ (pH 7.2)).

Figure 3:
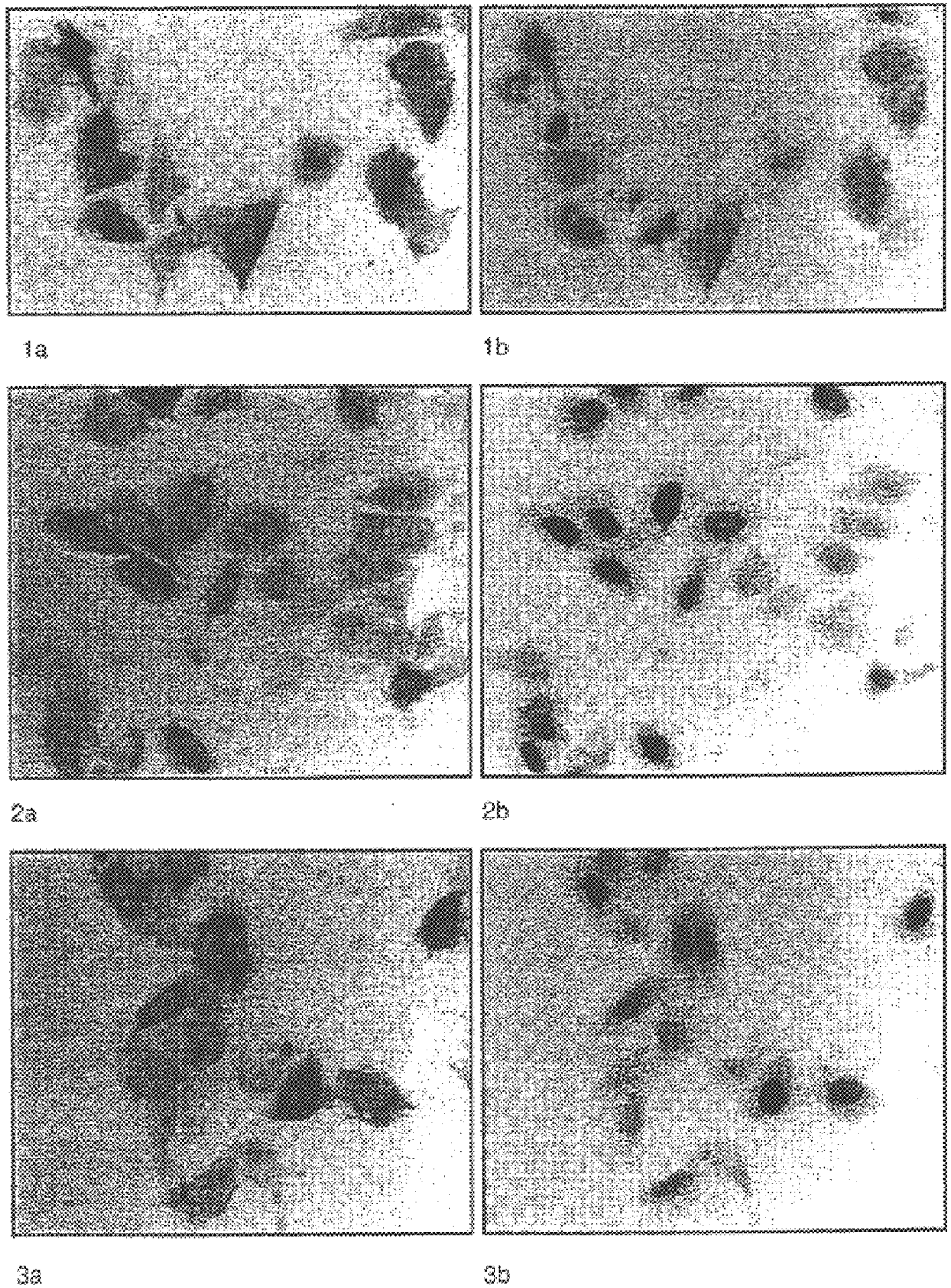
FIG. 3 is a fluorescent microscopic representation of NIH3T3-cells, microinjected into the cytoplasm with fluorescently labeled DNA with or without lac-repressor-NLS protein, as described in Example 6.

A mixture, consisting of DNA, bound to lac-repressor-mutants, and fluorescein-labeled BSA (BSA-FITC) was microinjected (Eppendorf Transjektor 5246 with Femtotips, diameter 0.5 $\mu$m, pressure of injection 55 hPa, time of injection 0.5 sec) into 50 NIH3T3-cells, respectively. Ten to 15 min after injection cells were analysed by fluorescence microscopy (FIG. 3). Following successful injection into the cytoplasm, BSA-FITC resides exclusively in the cytoplasm (1a, 2a, and 3a). Binding to lac-repressor-NLS-mutants results in nearly all cells, which could be analysed, in transport of the DNA into the nucleus within less than 15 min (NLS1-Dimer, 2b) and less than 10 min (NLS2-Dimer, 3 b), respectively, leaving nearly no DNA in the cytoplasm. Controls demonstrate that labeled DNA without binding proteins remains in the cytoplasm (1b).

EXAMPLE 7
Transfection with Lac-repressor-NLS

Figure 4:
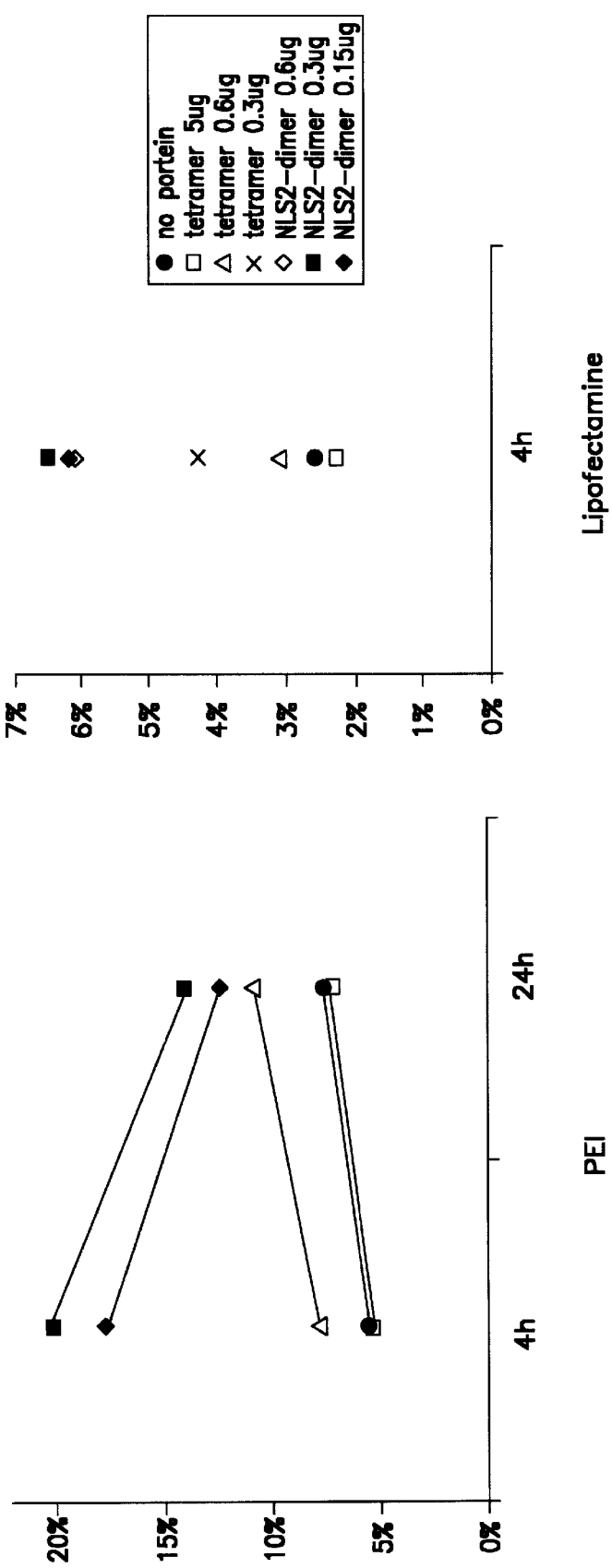
FIG. 4 is a graphic representation of transfection efficiencies with or without lac-repressor-NLS protein, shown as percent of transfected NIH3T3-cells, as described in Example 7.

One microgram of a linear DNA of 1.1 kb length, containing a complete expression-cassette and a polyadenylation sequence followed by a perfect palindromic lac-operator-sequence, was incubated in 50 $\mu$l isotonic 0.5× RPMI (for lipofection) or 150 mM NaCl (for transfection using polyethylenimine) for 30 min at room temperature with different concentrations of lac-repressor-protein (approx. 2.5 $\mu$g, 0.3 $\mu$g and 0.15 $\mu$g dimer, and 5 $\mu$g, 0.6 $\mu$g or 0.3 $\mu$g tetramer, respectively). The samples were complexed with Lipofectamine (Life Technologies) or Polyethylenimine (PEI, ExGen 500, Fermentas) according to the manufacturer's instructions and added to confluent NIH3T3-cells. The results are shown in FIG. 4.

Transfection efficiency, determined 4 hours past transfection, can be increased by the lac-repressor-NLS by a factor of 3–4. In the example described here, adherent NIH3T3 cells were cultivated to confluence before transfection, leading to an extensive inhibition of cell division. Four hours past transfection only a few cells have divided. The period in which the anyway limited division rate in this example becomes relevant for transfection, is additionally reduced by the fact that transfected DNA, which is taken up by endocytosis, has to leave the endosomes and subsequently the complex with the cationic transfection reagent, before it can be transported to the nucleus to be expressed. Lipofectamine-DNA-complexes probably persist noticeably longer than DNA-complexes with polyethylenimine, leading to a less clear effect of lac-represssor-NLS using Lipofectamine. After most of the cells have divided once 24 hours later, the expression rates of transfected DNA with and without a nuclear transport reagent approximate gradually.

REFERENCES

Batterson, W., Furlong, D. and Roizman, B. (1983) Molecular genetics of herpes simplex virus. VIII. further characterization of a temperature-sensitive mutant defective in release of viral DNA and in other stages of the viral reproductive cycle. J. Virol. 45: 397

Boulikas, T. (1993) Nuclear localization signals (NLS). Crit. Rev. Euk. Gene Expr. 3: 193

Boulikas, T. (1996) Nuclear import of protein kinases and cyclins. J. Cell. Biochem. 60: 61

Boulikas, T. (1997) Nuclear import of DNA repair proteins. Anticancer Res. 17: 843

Chen, Y.-R., Lees-Miller, S. P., Tegtmeyer, P. and Anderson, C. W. (1991) The human DNA-activated protein kinase phosphorylates simian virus 40 T antigen at amino- and carboxy-terminal sites. J. Virol. 65: 5131

Citovsky, V., Warnick, D., and Zambryski, P. (1994) Nuclear import of Agrobacterium VirD2 and VirE2 proteins in maize and tobacco. Proc. Natl. Acad. Sci. USA 91: 3210

Collas, P., Husebye, H. and Alestrőm, P. (1996) The nuclear localization sequence of the SV40 T antigen promotes transgene uptake and expression in zebrafish embryo nuclei. Transg. Res. 5: 451

Collas, P. and Alestrőm, P. (1996) Nuclear localization signal of SV40 T antigen directs import of plasmid DNA into sea urchin male pronuclei in vitro. Mol. Repr. Dev. 45: 431

Collas, P. and Alestrőm, P. (1997 a) Rapid targeting of plasmid DNA to zebrafish embryo nuclei by the nuclear localization signal of SV40 T antigen. Mol. Mar. Biol. Biotech. 6: 48

Collas, P. and Alestrőm, P. (1997 b) Nuclear localization signals: a driving force for nuclear transport of plasmid DNA in zebrafish. Biochem. Cell. Biol. 75:633

Dowty, M. E., Williams, P., Zhang, G., Hagstrom, J. E. and Wolff, J. A. (1995) Plasmid entry into postmitotic nuclei of primary rat myotubes. Proc. Natl. Acad. Sci. USA 92: 4572

Ellison, V. and Brown, P. O. (1994) A stable complex between integrase and viral DNA ends mediates human immunodeficiency virus integration in vitro. Proc. Natl. Acad. Sci. USA 91: 7316

Emi, N., Kidoaki, S., Yoshikawa, K., Saito, H. (1997) Gene transfer mediated by polyarginine requires a formation of big carrier-complex of DNA aggregate. Biochem. Biophys. Res. Commun. 231:421–424

Fieck, A., Wyborski, D. L. and Short, J. M. (1992) Modifications of the *E.coli* Lac repressor for expression in eukaryotic cells: effects of nuclear signal sequences on protein activity and nuclear accumulation. Nucl. Acids Res. 20: 1785

Friedmann, T. (1994) Gene therapy for neurological disorders. Trends in Genetics 10: 210

Friedmann, T. (1996) Human gene therapy—an immature genie, but certainly out of the bottle. Nature Med. 2: 144

Fritz, J. D., Herweijer, H., Zhang, G. and Wolff, J. A. (1996) Gene transfer into mammalian cells using histone-condensed plasmid DNA. Human gene therapy 7: 1395

Gallay, P., Stitt, V., Mundy, C., Oettinger, M., and Trono, D. (1996) Role of the karyopherin pathway in human immunodeficiency virus type 1 nuclear import. J. Virol. 70: 1027

Greber, U. F., Willetts, M., Webster, P., and Helenius, A. (1993) Stepwise dismantling of adenovirus 2 during entry into cells. Cell 75: 477

Görlich, D., Henklein, P., Laskey, R. A. and Hartmann, E. (1996) A 41 amino acid motif in importin-a confers binding to importin-b and hence transit into the nucleus. EMBO J. 15: 1810

Görlich D. (1998) Transport into and out of the cell nucleus. EMBO J. 17: 2721

Jans, D. A., Ackerfmann, M. J. Bischoff, J. R., Beach, D. H. and Peters, R. (1991) $p43^{cdc2}$-mediated phosphorylation at $T^{124}$ inhibits nuclear import of SV-40 T antigen proteins. J. Cell Biol. 115: 1203

Kaneda, Y., lwai, K., and Uchida, T. (1989) Increased expression of DNA cointroduced with nuclear protein in adult rat liver. Science 243: 375

Kolkhof, P. (1992) Specificities of three tight-binding Lac repressors. Nucl. Acids Res. 20: 5035

Lanford, R. E., Kanda, P., Kennedy, R. C. (1986) Induction of nuclear transport with a synthetic peptide homologous to the SV40 T antigen transport signal. Cell 46:575–582

Mistry, A. R., Falciola, L., Monaco, L., Tagliabue, R., Acerbis, G., Knight, A., Harbottle, R. P., Soria, M., Bianchi, M. E., Coutelle, C. and Hart, S. L. (1997) Recombinant HMG1 protein produced in pichia pastoris: a nonviral gene delivery agent. Biotechniques 22: 718

Nakanishi, A., Clever, J., Yamada, M., Li, P. P., and Kasamatsu, H. (1996) Association with capsid proteins promotes nuclear targeting of simian virus 40 DNA. Proc. Natl. Acad. Sci. USA 93: 96

Naldini, L., Blomer, U., Gallay, P., Ory, D., Mulligan, R., Gage, F. H., Verma, I. M., Trono, D. (1996) In vivo gene delivery and stable transduction of non-dividing cells by a lentiviral vector. Science 272: 263

Neumann, G., Castrucci, M. R. and Kawaoka, Y. (1997) Nuclear import and export of Influenca virus nucleoprotein. J. Virol. 71: 9690

Nielson, P., Egholm, M., Berg, R. H. and Buchardt, O. (1991) Sequence selective recognition of DNA by strand displacement with a thymine-sustituted polyamide. Science 254:1497

Niidome, T., Ohmori, N., Ichinose, A., Wada, A., Mihara, H., Hirayama, T., Aoyagi, H. (1997) Binding of cationic alpha-helical peptides to plasmid DNA and their gene transfer abilities into cells. J. Biol. Chem. 272:15307–15312

Rihs, H.-P. and Peters, R. (1989) Nuclear transport kinetics depend on phosphorylation-site-containing sequences flanking the karyophilic signal of the Simian virus 40 T antigen. EMBO J., 8: 1479

Rihs, H.-P., Jans, D. A., Fan, H. and Peters, R. (1991) The rate of nuclear cytoplasmic protein transport is determined by the casein kinase II site flanking the nuclear localization sequence of the SV40 T-antigen. EMBO J. 10: 633.

Shuman, S., (1994) Novel approach to molecular cloning and polynucleotide synthesis using vaccinia DNA topoisomerase. J. Biol. Chem. 269: 32678

Sebastyën, M. G., Ludtke, J. J., Bassik, M. C., Zhang, G., Budker, V., Lukhtanov, E. A., Hagstrom, J. E. and Wolff, J. A. (1998) DNA Vector chemistry: The covalent attachment of signal peptides to plasmid DNA. Nature Biotech. 16: 80

Sorgi, F. L., Bhattacharya, S., Huang, L. (1997) Protamine sulfate enhances lipid-mediated gene transfer. Gene Ther. 4:961–968

Trubetskoy, V. S., Budker, V. G., Hanson, L. J., Slattum, P. M., Wolff, J. A., Hagstrom, J. E. (1998) Self-assembly of DNA-polymer complexes using template polymerization. Nucleic Acids Res. 26:4178–4185

Wadhwa, M. S., Collard, W. T., Adami, R. C., McKenzie, D. L., Rice, K. G. (1997) Peptide-mediated gene delivery: influence of peptide structure on gene expression. Bioconjug. Chem. 8:81–88

Wang, P., Palese, P. and O'Neill, R. E. (1997) The NPI-1/NPI-3 (Karyopherin a) binding site on the Influenca A virus nucleoprotein is a nonconventional nuclear localisation signal. J. Virol. 71: 1850

Weiss, K., Ryder, U. and Lamond, A. I. (1997) The conserved amino-terminal domain of hSRP1a is essential for nuclear protein import. EMBO J. 15: 1818

Wilke, M., Fortunati, E., van den Broek, M., Hoogeveen, A. T. and Scholte, B. J. (1996) Efficacy of a peptide-based gene delivery system depends on mitotic activity. Gene Ther. 31:1133–1142

Xiao, C.-Y., Hübner, S. and Jans, D. A. (1997) SV40 large tumor antigen nuclear import is regulated by the double-stranded DNA-dependent protein kinase site (serine 120) flanking the nuclear localisation sequence. J. Biol. Chem. 272: 22191

Yoneda, Y., Arioka, T., Imamoto-Sonobe, N., Sugawa, H., Shimonishi, Y., Uchida, T. (1987) Synthetic peptides containing a region of SV 40 large T-antigen involved in nuclear localization direct the transport of proteins into the nucleus. Exp. Cell Res. 170:439–452

Yoneda, Y., Semba, T., Kaneda. Y., Noble, R. L., Matsuoka, Y., Kurihara, T., Okada, Y. and Imamoto, N. (1992) A long synthetic peptide containing a nuclear localization signal and its flanking sequences of SV40 T-antigen directs the transport of IgM into the nucleus effectively. Exp. Cell Res. 201:313

PATENTS CITED

Dzau, V. J. and Kaneda, Y. (1997) Method for producing in vivo delivery of therapeutic agents via liposome. N no.: 5631237

Gerhard, F., Kuhn C-S., Mittenbühler, K. und Appel K. (Offenlegungsschrift vom 15. 5. 1997) DE 195 41 679 A1

Gopal, T. V. (1997) Peptide-mediated gene transfer U.S. Pat. No. 5,670,347

Hawley-Nelson, P., Lan, J., Shih, P. J., Jessee, J. A. and Schifferli, K. P. (1998) Peptide-enhanced cationic lipid transfections. U.S. Pat. No. 5,736,392

Nielson, P. E., Buchardt, O. Egholm, M., and Berg, R. H. (1996) Peptide Nucleic acids. U.S Pat. No. 5,539,082

Szoka, F. C. Jr. Self-assembling polynucleotide delivery system. (PCT vom 14. 10. 1993) WO 93/19768., therein: claims 23 to 27.

SEQUENCE LISTING

```
<160> NUMBER OF SEQ ID NOS: 15

<210> SEQ ID NO 1
<211> LENGTH: 21
<212> TYPE: PRT
<213> ORGANISM: Artificial Sequence
<220> FEATURE:
<223> OTHER INFORMATION: SV21

<400> SEQUENCE: 1

Gly Lys Pro Thr Ala Asp Asp Gln His Ser Thr Pro Pro Lys Lys Lys
1               5                   10                  15

Arg Lys Val Glu Asp
            20

<210> SEQ ID NO 2
<211> LENGTH: 27
<212> TYPE: PRT
<213> ORGANISM: Artificial Sequence
<220> FEATURE:
<223> OTHER INFORMATION: SV27

<400> SEQUENCE: 2

Gly Lys Pro Ser Ser Asp Asp Glu Ala Thr Ala Asp Ser Gln His Ser
1               5                   10                  15

Thr Pro Pro Lys Lys Lys Arg Lys Val Glu Asp
            20                  25

<210> SEQ ID NO 3
<211> LENGTH: 13
<212> TYPE: DNA
<213> ORGANISM: Artificial Sequence
<220> FEATURE:
<223> OTHER INFORMATION: DNA is PNA (peptide nucleic acid)

<400> SEQUENCE: 3
cctttctccc ttc                                                      13

<210> SEQ ID NO 4
<211> LENGTH: 13
<212> TYPE: DNA
<213> ORGANISM: Artificial Sequence
<220> FEATURE:
<223> OTHER INFORMATION: DNA is PNA (peptide nucleic acid)

<400> SEQUENCE: 4
ctcttccttt ttc                                                      13

<210> SEQ ID NO 5
<211> LENGTH: 5
<212> TYPE: DNA
<213> ORGANISM: Artificial Sequence
```

```
<220> FEATURE:
<223> OTHER INFORMATION: DNA is PNA; mixed peptide/PNA sequence

<400> SEQUENCE: 5 ccttt                                                               5

<210> SEQ ID NO 6
<211> LENGTH: 13
<212> TYPE: DNA
<213> ORGANISM: Artificial Sequence
<220> FEATURE:
<223> OTHER INFORMATION: DNA is PNA

<400> SEQUENCE: 6 ctcttcctttt ttc                                                     13

<210> SEQ ID NO 7
<211> LENGTH: 67
<212> TYPE: PRT
<213> ORGANISM: Artificial Sequence
<220> FEATURE:
<223> OTHER INFORMATION: PNA-NLS

<400> SEQUENCE: 7

Ala Glu Glu Ala Ala Glu Glu Ala Ala Glu Glu Ala Ala Glu Glu Ala
1               5                   10                  15

Ala Glu Glu Ala Ala Glu Glu Ala Ala Glu Glu Ala Ala Glu Glu Ala
            20                  25                  30

Ala Glu Glu Ala Ala Glu Glu Ala Gly Lys Pro Ser Ser Asp Asp Glu
        35                  40                  45

Ala Thr Ala Asp Ser Gln His Ser Thr Pro Pro Lys Lys Lys Arg Lys
    50                  55                  60

Val Glu Asp
65

<210> SEQ ID NO 8
<211> LENGTH: 8
<212> TYPE: PRT
<213> ORGANISM: Artificial Sequence
<220> FEATURE:
<223> OTHER INFORMATION: Sequence corresponding to the NLS of the SV40
      virus large T antigen

<400> SEQUENCE: 8

Met Pro Lys Lys Lys Arg Lys Val
1               5

<210> SEQ ID NO 9
<211> LENGTH: 16
<212> TYPE: PRT
<213> ORGANISM: Artificial Sequence
<220> FEATURE:
<223> OTHER INFORMATION: Sequence corresponds to a neutral hybrid
      consisting of the SV40 N LS and the N-terminal flanking region of
      the NLS from polyoma virus VP2 protein

<400> SEQUENCE: 9

Met Glu Glu Asp Thr Pro Pro Lys Lys Lys Arg Lys Val Glu Asp Leu
1               5                   10                  15
```

```
<210> SEQ ID NO 10
<211> LENGTH: 7
<212> TYPE: PRT
<213> ORGANISM: Artificial Sequence
<220> FEATURE:
<223> OTHER INFORMATION: DNA is PNA; mixed peptide/PNA sequence

<400> SEQUENCE: 10

Gly Gly Gly Gly Gly Gly Gly
1               5

<210> SEQ ID NO 11
<211> LENGTH: 5
<212> TYPE: DNA
<213> ORGANISM: Artificial Sequence
<220> FEATURE:
<223> OTHER INFORMATION: DNA is PNA; mixed peptide/PNA sequence

<400> SEQUENCE: 11 tttcc                                                                        5

<210> SEQ ID NO 12
<211> LENGTH: 10
<212> TYPE: PRT
<213> ORGANISM: Artificial Sequence
<220> FEATURE:
<223> OTHER INFORMATION: sequence corresponds to the NLS of the SV40
      virus large T antigen

<400> SEQUENCE: 12

Met Lys Pro Val Thr Leu Tyr Asp Val Ala
1               5                   10

<210> SEQ ID NO 13
<211> LENGTH: 9
<212> TYPE: PRT
<213> ORGANISM: Artificial Sequence
<220> FEATURE:
<223> OTHER INFORMATION: sequence corresponds to a neutral hybrid
      consisting of the SV40 N LS and the N-terminal flanking region of
      the NLS from polyoma virus VP2 protein

<400> SEQUENCE: 13

Lys Pro Val Thr Leu Tyr Asp Val Ala
1               5

<210> SEQ ID NO 14
<211> LENGTH: 21
<212> TYPE: DNA
<213> ORGANISM: Artificial Sequence
<220> FEATURE:
<223> OTHER INFORMATION: lac-operator-sequence

<400> SEQUENCE: 14
aattgtgagc ggataacaat t                                                     21

<210> SEQ ID NO 15
<211> LENGTH: 20
<212> TYPE: DNA
<213> ORGANISM: Artificial Sequence
<220> FEATURE:
<223> OTHER INFORMATION: lac-operator-sequence

<400> SEQUENCE: 15
aattgtgagc gctcacaatt                                                       20
```

What is claimed is:

1. A nuclear transport agent for transferring a nucleic acid from cytoplasm into a nucleus of a eukaryotic cell comprising a first module and a second module, wherein the first module is module A that binds specifically to a DNA molecule so as not to form complexes consisting of more than one DNA molecule, and wherein the second module is module B that comprises an extended nuclear localization signal having a charge thus preventing the second module from mediating nonspecific binding of the nuclear transport agent to the DNA molecule.

2. The nuclear transport agent of claim 1, wherein the first module specifically binds a sequence of the DNA molecule.

3. The nuclear transport agent of claim 1, wherein the first module specifically binds a terminal sequence of the DNA molecule.

4. The nuclear transport agent of claim 3, wherein the first module specifically binds covalently to the terminal sequence of the DNA molecule.

5. The nuclear transport agent of claim 1, wherein the first module comprises a synthetic peptide, a protein, a peptide nucleic acid, or a recombinant protein that specifically binds to the DNA molecule.

6. The nuclear transport agent of claim 1, wherein the second module comprises an extended nuclear localization signal having a substantially neutral net charge, wherein the charge facilitates nuclear transport of the nucleic acid.

7. The nuclear transport agent of claim 1, wherein the second module comprises an extended nuclear localization signal comprising a nuclear localization signal and flanking amino acids having a substantially negative charge.

8. The nuclear transport agent of claim 7, wherein the extended nuclear localization signal comprises from about 2 to about 40 flanking amino acids.

9. The nuclear transport agent of claim 8, wherein the extended nuclear localization signal comprises from about 4 to about 20 flanking amino acids.

10. The nuclear transport agent of claim 1, wherein the second module further comprises a spacer consisting of one or more peptide sequences or non-peptide sequences, wherein the sequences are external to the nuclear localization signal.

11. The nuclear transport agent of claim 10, wherein the spacer separates the nuclear localization signal from the first module.

12. The nuclear transport agent of claim 1, wherein the first module is a protein that binds to DNA in a sequence specific manner and the second module further comprises a non nuclear localization signal.

13. The nuclear transport agent of claim 12, wherein the non nuclear localization signal facilitates transport of the DNA molecule into or within the cell.

14. A gene transfer system comprising a nuclear transport agent according to claim 1 and further comprising a cationic lipid, a peptide, a polyamine, or a cationic polymer.

15. (A) An in vitro method for transporting a DNA molecule into a nucleus of a eukaryotic cell comprising:

transfecting the cell with the DNA molecule and a nuclear transport agent of claim 1 and contacting the DNA molecule with the nuclear transport agent, wherein the DNA transport to the nucleus is facilitated via the nuclear transport agent.

16. The method of claim 15, wherein the eukaryotic cell is a primary cell.

* * * * *